United States Patent
Vesole et al.

(10) Patent No.: US 12,236,801 B2
(45) Date of Patent: Feb. 25, 2025

(54) INJECTION TRAINING DEVICE AND METHOD FOR USING SAME

(71) Applicant: Janssen Biotech, Inc., Horsham, PA (US)

(72) Inventors: Steven Vesole, Redwood City, CA (US); Hung Mach, Warren, NJ (US); Keith D. Brown, Warren, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 911 days.

(21) Appl. No.: 17/227,632

(22) Filed: Apr. 12, 2021

(65) Prior Publication Data

US 2021/0327302 A1    Oct. 21, 2021

Related U.S. Application Data

(60) Provisional application No. 63/011,154, filed on Apr. 16, 2020.

(51) Int. Cl.
*G09B 23/28*    (2006.01)

(52) U.S. Cl.
CPC .................................. *G09B 23/285* (2013.01)

(58) Field of Classification Search
CPC .............................. G09B 23/28; G09B 23/285
USPC .......................................................... 434/262
See application file for complete search history.

(56) References Cited

U.S. PATENT DOCUMENTS

| | | |
|---|---|---|
| 3,318,021 A | 5/1967 | Sarnoff |
| 3,426,448 A | 2/1969 | Sarnoff |
| D323,031 S | 1/1992 | Ahlstrand et al. |
| D383,205 S | 9/1997 | Pagay et al. |
| D412,206 S | 7/1999 | Basile et al. |
| D578,210 S | 10/2008 | Muta et al. |
| D610,678 S | 2/2010 | Kawamura |
| 7,682,155 B2 | 3/2010 | Raven et al. |
| D618,347 S | 6/2010 | Bradshaw |
| D638,122 S | 5/2011 | Kosinski et al. |
| D638,123 S | 5/2011 | Kosinski et al. |
| D638,538 S | 5/2011 | Kosinski et al. |
| D702,834 S | 4/2014 | Norton et al. |
| 8,714,984 B2 * | 5/2014 | Mach ..................... A61M 5/20 434/272 |
| 9,050,423 B2 | 6/2015 | Peethambaran |
| D739,524 S | 9/2015 | Zemel et al. |
| D747,797 S | 1/2016 | Fourt et al. |

(Continued)

FOREIGN PATENT DOCUMENTS

| | | |
|---|---|---|
| EP | 2180459 A1 | 4/2010 |
| EP | 2351003 A1 | 8/2011 |

(Continued)

OTHER PUBLICATIONS

International Search Report for PCT/IB2021/052996 dated Jun. 30, 2021.

*Primary Examiner* — Joseph B Baldori
(74) *Attorney, Agent, or Firm* — Craig M. Brown (57) ABSTRACT

An injection training device is configured to simulate the tactile sensations and forces associated with the operation of a corresponding injection device. However, the injection training device does not carry the medication or a needle. The injection training device includes a plunger that is depressed to drive a rotor to rotate. A viscous fluid resists rotation of the rotor, which thereby resists depression of the plunger.

21 Claims, 8 Drawing Sheets

(56) References Cited

U.S. PATENT DOCUMENTS

| | | | |
|---|---|---|---|
| D747,799 S | 1/2016 | Norton et al. | |
| 9,336,690 B2 | 5/2016 | Helmer et al. | |
| 9,443,445 B2 | 9/2016 | Laurusonis et al. | |
| 9,489,868 B2 | 11/2016 | Smith et al. | |
| D775,324 S | 12/2016 | Larson et al. | |
| D775,325 S | 12/2016 | Larson et al. | |
| D789,520 S | 6/2017 | Tseng et al. | |
| 9,802,002 B2 | 10/2017 | Smith | |
| 9,805,621 B2 | 10/2017 | Baker et al. | |
| 10,083,630 B2 | 9/2018 | Samosky et al. | |
| 10,235,904 B2 | 3/2019 | Rios et al. | |
| 10,269,266 B2 | 4/2019 | Rios et al. | |
| D855,176 S | 7/2019 | Yang et al. | |
| 10,417,937 B2 | 9/2019 | Gaillot et al. | |
| D867,583 S | 11/2019 | Yang et al. | |
| 10,500,340 B2 | 12/2019 | Rios et al. | |
| 2014/0127661 A1 | 5/2014 | Yokoi | |
| 2015/0235571 A1 | 8/2015 | Alexandersson | |
| 2015/0248848 A1 | 9/2015 | Yokoi et al. | |
| 2016/0335920 A1* | 11/2016 | Bendek | G09B 23/285 |
| 2016/0367766 A1 | 12/2016 | Baker et al. | |
| 2018/0005547 A1 | 1/2018 | Baker et al. | |
| 2018/0182263 A1 | 6/2018 | Krulevitch et al. | |
| 2018/0190153 A1 | 7/2018 | Krulevitch et al. | |
| 2018/0190154 A1 | 7/2018 | Krulevitch et al. | |
| 2018/0233066 A1 | 8/2018 | Lettman et al. | |
| 2018/0240364 A1 | 8/2018 | Baker et al. | |
| 2018/0243513 A1 | 8/2018 | Rolfs et al. | |
| 2018/0357928 A1 | 12/2018 | Baker et al. | |
| 2019/0043386 A1 | 2/2019 | Krulevitch et al. | |
| 2019/0096286 A1 | 3/2019 | Chang et al. | |
| 2019/0189029 A1 | 6/2019 | Bostrom | |
| 2020/0043372 A1 | 2/2020 | Basile et al. | |
| 2020/0043373 A1 | 2/2020 | Baker et al. | |
| 2020/0101227 A1 | 4/2020 | Mach | |
| 2020/0168124 A1* | 5/2020 | Baker | A61M 5/31511 |
| 2021/0049930 A1* | 2/2021 | Mortimer | A61M 11/007 |
| 2021/0113776 A1* | 4/2021 | Hopkins | A61M 5/31511 |

FOREIGN PATENT DOCUMENTS

| | | | |
|---|---|---|---|
| EP | 2649605 A1 | 10/2013 | |
| EP | 1946286 A4 | 5/2014 | |
| EP | 2784766 A1 | 10/2014 | |
| EP | 2456492 A4 | 11/2014 | |
| EP | 2820640 B1 | 5/2016 | |
| EP | 2577646 B1 | 9/2016 | |
| EP | 2736030 B1 | 9/2017 | |
| EP | 3311373 A1 | 4/2018 | |
| EP | 3311376 A1 | 4/2018 | |
| EP | 3251109 A4 | 7/2018 | |
| EP | 3341056 A1 | 7/2018 | |
| EP | 3365049 A2 | 8/2018 | |
| EP | 3227880 B1 | 9/2018 | |
| EP | 2979263 B1 | 12/2018 | |
| EP | 3469573 A1 | 4/2019 | |
| EP | 3433846 A4 | 9/2019 | |
| EP | 3580738 A2 | 12/2019 | |
| EP | 3596721 A1 | 1/2020 | |
| EP | 3602528 A2 | 2/2020 | |
| EP | 3335213 B1 | 5/2020 | |
| EP | 3311374 B1 | 7/2020 | |
| EP | 3427244 B1 | 9/2020 | |
| EP | 3311375 B1 | 3/2021 | |
| RU | 2687564 C1 | 5/2019 | |
| WO | WO 2007/056231 A3 | 5/2007 | |
| WO | WO 2010/046319 A1 | 4/2010 | |
| WO | WO 2011/024188 A4 | 3/2011 | |
| WO | WO 2011/151315 A1 | 12/2011 | |
| WO | WO 2012/076494 A1 | 6/2012 | |
| WO | WO 2013/012055 A1 | 1/2013 | |
| WO | WO 2013/130973 A1 | 9/2013 | |
| WO | WO 2014/154795 A1 | 10/2014 | |
| WO | WO 2016/089706 A1 | 6/2016 | |
| WO | WO 2016/123144 A3 | 8/2016 | |
| WO | WO 2016/203058 A1 | 12/2016 | |
| WO | WO 2016/203059 A1 | 12/2016 | |
| WO | WO 2016/204795 A1 | 12/2016 | |
| WO | WO2016/207119 | 12/2016 | |
| WO | WO 2017/004566 A1 | 1/2017 | |
| WO | WO 2017/027753 A1 | 2/2017 | |
| WO | WO 2017/034618 A1 | 3/2017 | |
| WO | WO 2017/070391 | 4/2017 | |
| WO | WO 2017/153077 A1 | 9/2017 | |
| WO | WO 2017/164927 A1 | 9/2017 | |
| WO | WO 2017/211531 A1 | 12/2017 | |
| WO | WO 2018/007448 A1 | 1/2018 | |
| WO | WO 2018/075335 A1 | 4/2018 | |
| WO | WO 2018/136901 A1 | 7/2018 | |
| WO | WO 2018/148337 | 8/2018 | |
| WO | WO 2018/183772 | 10/2018 | |
| WO | WO 2019/006210 A1 | 1/2019 | |
| WO | WO 2019/023252 A1 | 1/2019 | |
| WO | WO 2019/090217 A1 | 5/2019 | |
| WO | 2019142007 | 7/2019 | |
| WO | WO 2020/006400 A1 | 1/2020 | |
| WO | WO 2020/026927 A1 | 2/2020 | |

* cited by examiner

INJECTION TRAINING DEVICE AND METHOD FOR USING SAME

CROSS-REFERENCE TO RELATED APPLICATIONS

This application claims priority to U.S. Patent Application Ser. No. 63/011,154 filed Apr. 16, 2020, the disclosure of which is hereby incorporated by reference as if set forth in its entirety herein.

BACKGROUND

Many medications are delivered by way of injection into the human body. In particular, an injection device typically includes a barrel that contains the medication, a needle attached to the barrel, and a plunger that is depressed in the barrel so as to drive the medication out of the barrel and through the needle. Different medications can be delivered using different injection techniques. In some instances, the plunger can be quickly depressed to deliver the full dosage of medication. However, in other instances, the injection process can be designed to occur over a longer time duration. For instance, some medications may have a high viscosity that resists depression of the plunger. Thus, the user will experience more resistance than the user may be accustomed to when injecting the medication.

Some medications are designed to be delivered via injection by a doctor, nurse, or other care provider at a care center. Other medications are indicated to be delivered via injection at home. Whether the person injecting the medication has substantial experience injecting medications that provide resistance to depressing the plunger or a patient or some other person who lacks such experience, it can be therefore desirable to provide an injection training device that simulates the tactile sensations of injecting a high-viscosity medication. Such an injection training device can allow the user to draw from his or her experience gained operating the injection training device when it comes time to deliver the medication through a syringe and needle.

SUMMARY

In one example, an injection training device can include a barrel, and a first assembly that includes a plunger and a damper housing coupled to the plunger. The first assembly can be translatable with respect to the barrel. The injection training device can further include a second assembly including a rotor, such that a damper chamber is defined between the rotor and the damper housing. A viscous fluid can be disposed in the damper chamber. Translation of the first assembly can cause a force to be applied to the rotor that causes the rotor to rotate about an axis of rotation with respect to the damper housing. The viscous fluid resists rotation of the rotor about the axis with respect to the damper housing.

In another example, a method of operating an injection training device can include the step of depressing a plunger in a distal direction with respect to a barrel, thereby causing the plunger to apply a force to a rotor that drives the rotor to travel in the distal direction. The method can further include, in response to the depressing step, rotating the rotor within a damper housing in a first direction of rotation about an axis, and providing a rotational counterforce to the rotation of the rotor with a viscous fluid disposed in a damper chamber between the rotor and the damper housing.

In still another example, an injection device can include a barrel, and a first assembly that includes a plunger and a damper housing coupled to the plunger. The first assembly can be translatable with respect to the barrel. The injection device can further include a second assembly including a rotor, such that a damper chamber is defined between the rotor and the damper housing. A viscous fluid can be disposed in the damper chamber. Translation of the first assembly can cause a force to be applied to the rotor that causes the rotor to rotate about an axis of rotation with respect to the damper housing. The viscous fluid resists rotation of the rotor about the axis with respect to the damper housing.

BRIEF DESCRIPTION OF THE DRAWINGS

The following detailed description will be better understood when read in conjunction with the appended drawings, in which there is shown in the drawings example embodiments for the purposes of illustration. It should be understood, however, that the present disclosure is not limited to the precise arrangements and instrumentalities shown. In the drawings.

DETAILED DESCRIPTION

Figures 1A, 1B:
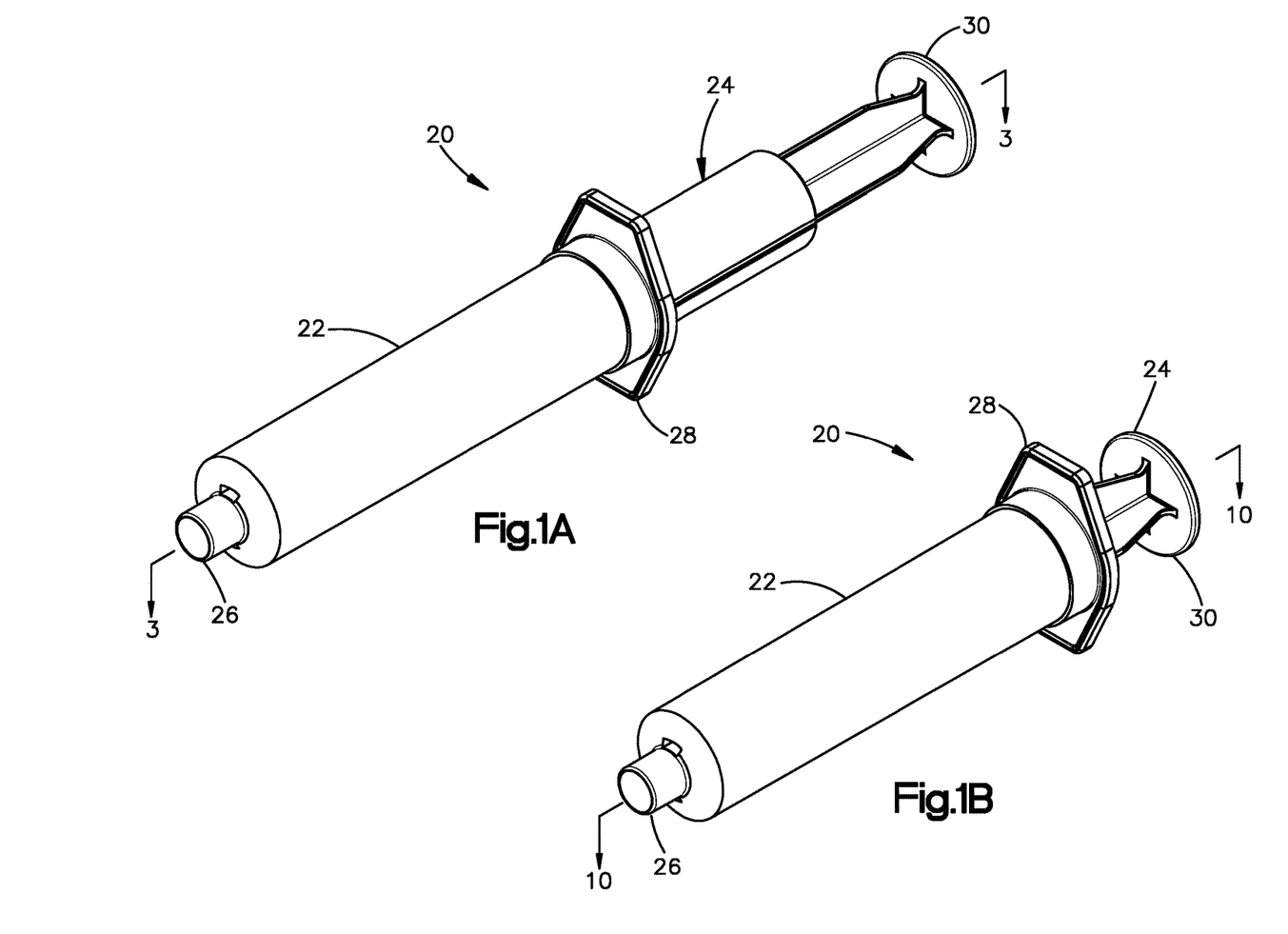
FIG. 1A is a perspective view of an injection training device shown in an initial undeployed position.
FIG. 1B is a perspective view of the injection training device shown in FIG. 1A, shown in a final deployed position.

Referring initially to FIGS. 1A-1B, an injection training device 20 is configured to simulate the tactile sensations and forces associated with the operation of a corresponding injection device that delivers a medication to a patient. The injection training device 20 includes a barrel 22 and a plunger 24 that is configured to be depressed in a distal direction from an initial or undeployed position shown in FIG. 1A to a final or deployed position shown in FIG. 1B. It is appreciated that the barrel of an injection device typically contains a medication that is delivered from the barrel to a needle or other suitable delivery member. However, the barrel of the injection training device 20 does not contain medication in some examples. Rather, the injection training device 20 is configured to simulate operation of an injection device without actually delivering medication.

The barrel 22 defines a proximal end 22a and a distal end 22b. The distal end 22b can define a simulated Luer lock connection 26. In this regard, it is recognized that injection devices typically include a needle, infusion set, or the like, that is attached to a barrel via a Luer lock. However, the simulated Luer lock connection 26 is not configured to attach to a needle, infusion set, or the like, but rather simulates the look of a Luer lock of the corresponding injection device. Alternatively, the injection training device 20 can include a simulated needle that extends out from the distal end 22b of the barrel 22, or any suitable alternative structure that extends out from the distal end 22b. Recognizing that the simulated Leur lock, simulated needle, or other structure that extends out from the distal end 22b primarily provides aesthetics, it is recognized that the injection training device 20 can alternatively be devoid of structure that extends out from the distal end 22b.

As will be appreciated from the description below, the injection training device 20 is configured to provide resistance to the depression of the plunger 24. The resistance to the depression of the plunger at a constant predetermined rate can be substantially equal to the resistance that a user will experience when delivering a medication from the corresponding injection device at the constant predetermined rate. Examples of the injection training device 20 can be configured to simulate a large volume subcutaneous injection. For instance, embodiments of the injection training device 20 can be configured to simulate the injection of a Darzalex Faspro™ (daratumumab and hyaluronidase-fihj) subcutaneous formulation marketed by Janssen Pharmaceuticals, Inc. having a place of business in Raritan, NJ It will be appreciated from the description below, however, that the injection training device 20 can be tuned to simulate delivery of other medications.

In one example, the desired stroke time to move the plunger from the initial or undeployed position to the final or deployed position can be in the range of approximately 3 minutes to approximately 5 minutes, such as approximately 4 minutes, though any suitable alternative stroke time can be achieved as desired. It is appreciated, however, that the user of the injection training device 20 can apply any suitable force as desired to depress the plunger. Further, the user of the injection training device 20 can depress the plunger over a range of possible time durations that can be the same as that to fully deliver the dosage of medication from the corresponding injection device, or different than that to fully deliver the dosage of medication from the corresponding injection device. The injection training device 20 provides the user with tactile feedback so as to allow the user to practice depressing the plunger at the constant predetermined rate that will allow the medication to be delivered to the patient from the corresponding injection device at a rate is designed to fully deliver the medication efficiently but with minimal pain to the patient. The corresponding injection device can include any suitable volume of medication in its barrel as desired, such as approximately 15 ml.

Ergonomically, the injection training device 20 is designed to simulate the corresponding injection device. For instance, the injection training device 20 can include a barrel flange 28 that extends out from the proximal end 22a of the barrel 22, and a plunger flange 30 that extends out from a proximal end of the plunger 24. The user can brace his or her fingers against the barrel flange 28 as the user applies a deployment force to the plunger 24 via his or her thumb in a distal direction, and in particular to the plunger flange 30, that drives the plunger to translate in the distal direction. Each of the components of the injection training device 20 defines a proximal end and a distal end that is opposite the proximal end in the distal direction. Further, the proximal end of each of the components is spaced from the distal end in a proximal direction that is opposite the distal direction.

Figure 2:
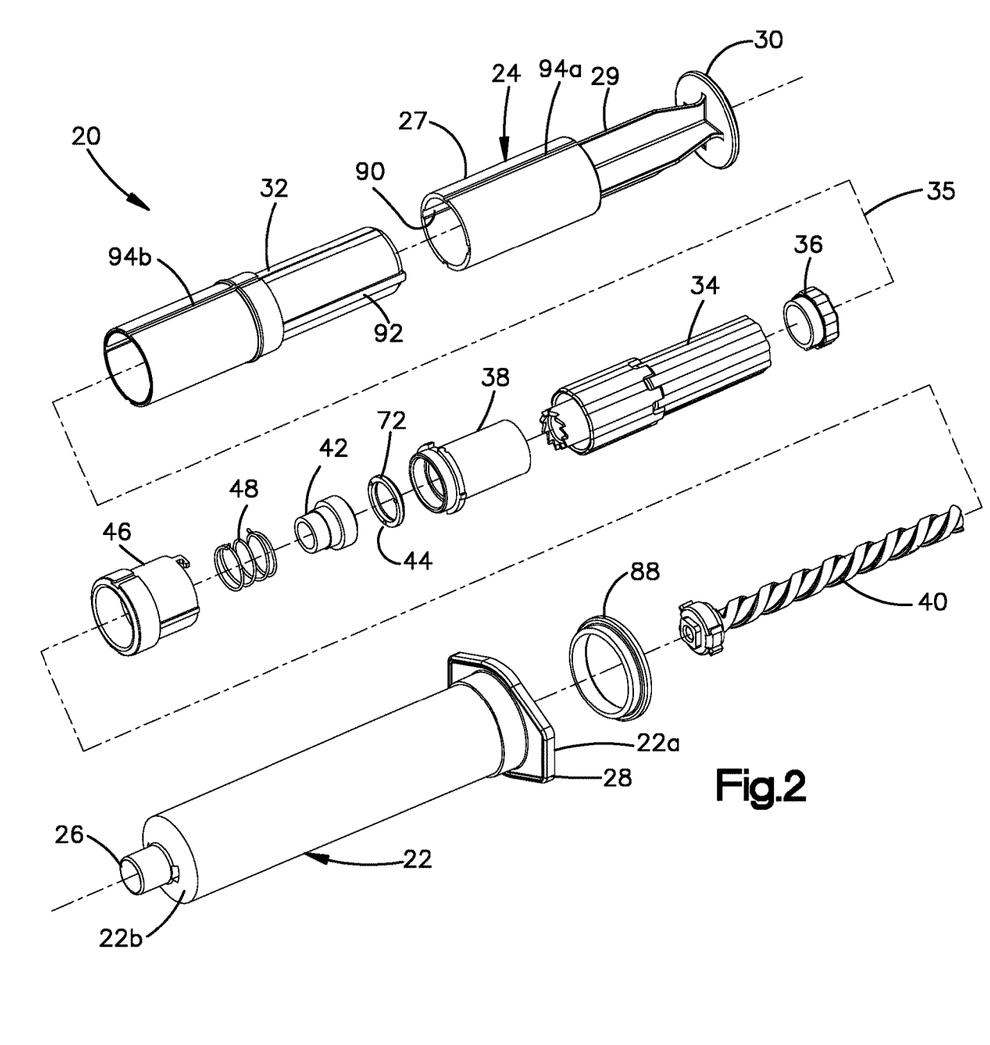
FIG. 2 is an exploded perspective view of the injection training device shown in FIG. 1A.

Referring now to FIG. 2, the components of the injection training device 20 will now be described. In particular, the injection training device 20 includes the barrel 22 and the plunger 24 as described above. The injection training device 20 further includes a damper housing 32 and a rotor 34 that is designed to rotate in the damper housing 32 about an axis of rotation 35 that is oriented in the proximal and distal directions. The injection training device 20 can further include a rotor cap 36 that is configured to attach to the rotor 34, for instance at the proximal end of the rotor 34. The injection training device 20 can further include a rotor retainer cap 38 that is configured to attach to the damper housing 32 and a sealing gasket 44 that are configured to seal an interface between the rotor retainer cap 38 and the rotor 34. The injection training device 20 can further include a shaft 40 that is configured to be supported in the barrel 22, and a clutch 42 that is configured to mate with the shaft 40 and engage the rotor 34. In one example, the shaft 40 can be configured as a threaded shaft that is threadedly mated with the clutch 42. For instance, the clutch 42 can rotatably fix to the rotor 34. The injection training device 20 can further include a damper housing cap 46 that is configured to extend in the distal direction from the rotor retainer cap 38. The injection training device 20 can further include a biasing member 48, such as a coil spring, an elastomer, or the like, that extends from the damper housing cap 46 to the clutch 42, and can bias the clutch 42 against the distal end of the rotor 34.

It is recognized that each of the components of the injection training device 20 can be configured as annular components that surround the axis 35 that can be said to extend along an axial direction. The axial direction can include both the proximal direction and the distal direction. Further, it should be appreciated that while the components of the injection training device 20 have been described as separate components, some of the components can instead define a single monolithic component. Conversely, while some of the components have been described as single unitary components, the components can alternatively be defined by two separate components that are attached to each other.

Figure 3:
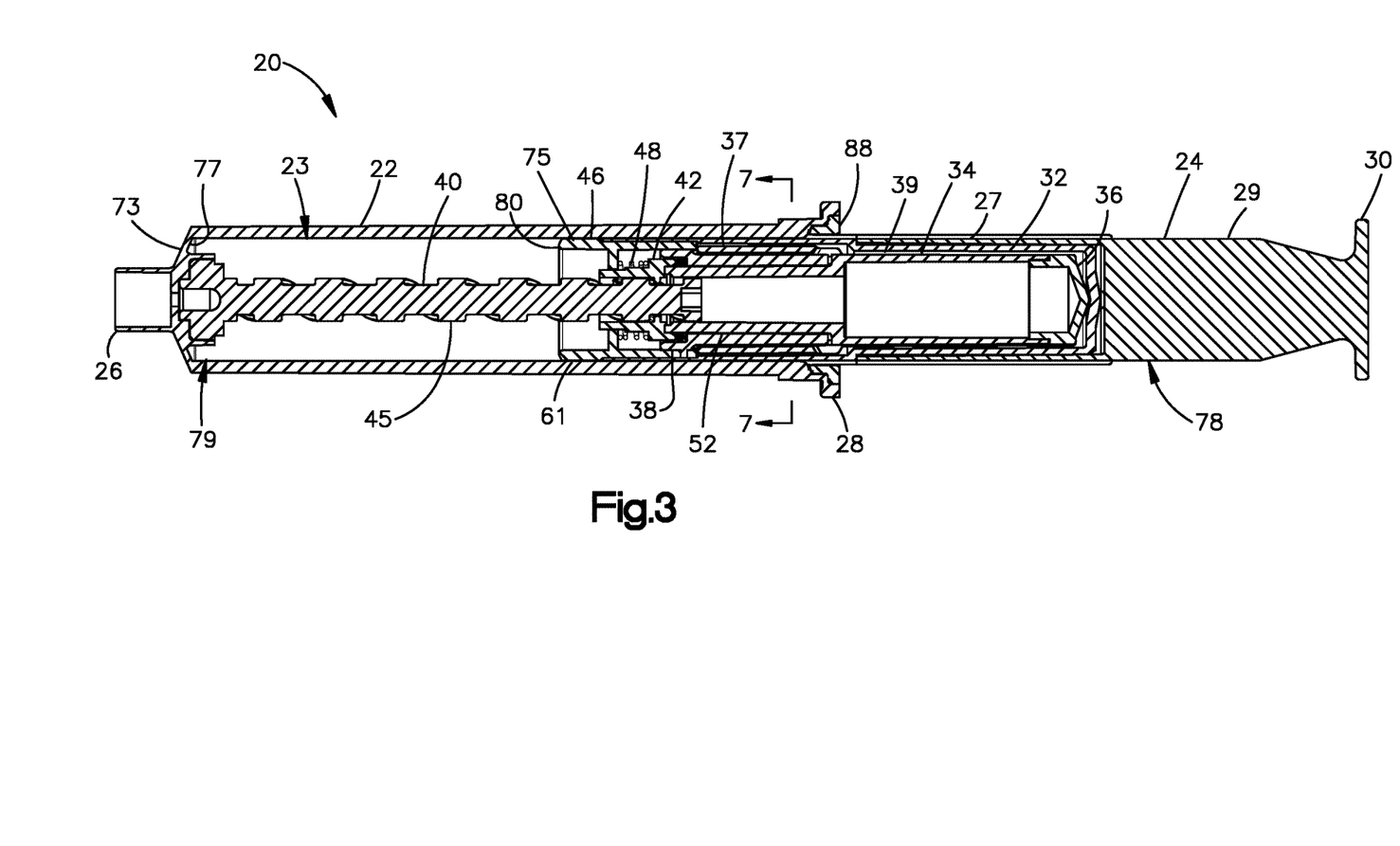
FIG. 3 is a sectional side elevation view of the injection training device in the initial undeployed position as shown in FIG. 1A.
Figure 4:
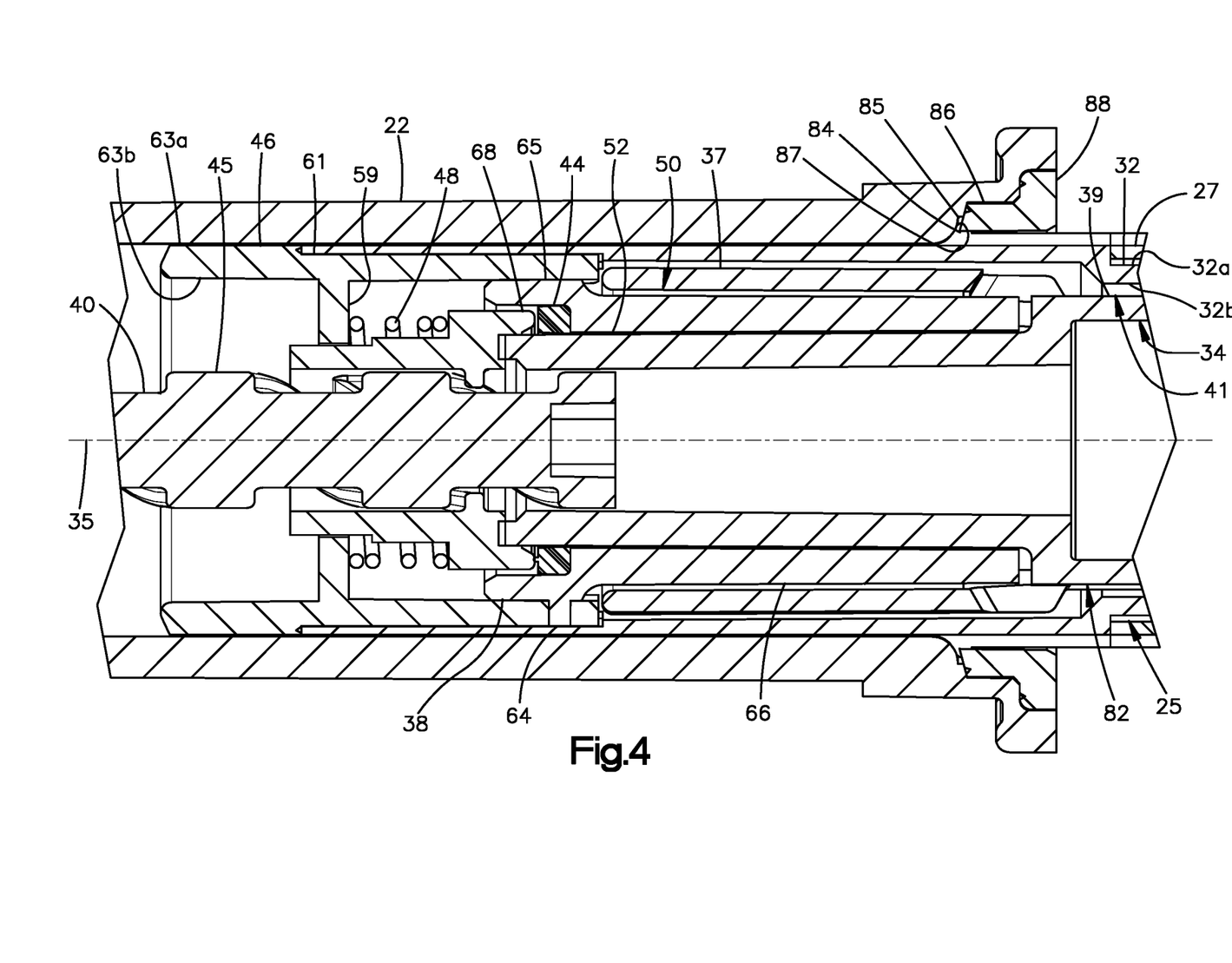
FIG. 4 is an enlarged sectional side elevation view of a portion of the injection training device shown in FIG. 3.

Referring now to FIGS. 2-4, the barrel 22 defines an internal barrel void 23, and the plunger 24 defines an internal plunger void 25. The damper housing 32 can extend into each of the internal barrel void 23 and the internal plunger void 25 when the plunger is in the undeployed position. The internal barrel void 23 can be disposed distal of the internal plunger void 25. The plunger 24 can extend out from the barrel void 23 in the undeployed position, and is configured to translate in the distal direction in the internal barrel void 23 toward the deployed position. The plunger 24 can define an annular plunger body 27, and a handle portion 29 that extends from the plunger body in the proximal direction. The plunger flange 30 can extend radially out from the proximal end of the handle portion 29.

The damper housing 32 can be disposed in the annular plunger body 27. The damper housing 32 can be configured as an annular body having a radially outer surface 32a and a radially inner surface 32b that is opposite the radially outer surface 32a. The radially inner surface 32b can face the rotor 34. A proximal portion of the radially outer surface 32a can face a radially inner wall of the plunger body 27, and a distal portion of the radially outer surface 32a can face a radially inner wall of the barrel 22. In this regard, the injection training device 20 can define a radially outward direction that extends away from the axis 35, and a radially inward direction that extends toward the axis 35. The damper housing 32 can be translatably coupled to the plunger 24, such that the damper housing 32 travels along with the plunger 24 in each of the distal direction and in the proximal direction.

The rotor 34 can be at least partially or entirely disposed in the damper housing 32. The rotor 34 defines a radially outer wall 37 having a radially outer surface 39 that faces the radially inner surface 32b of the damper housing 32. The rotor 34 is configured to rotate with respect to the damper housing 32 about the axis 35. For instance, when the plunger 24 is depressed in the distal direction, the rotor rotates about the axis 35 in a first direction of rotation. The injection training device 20 can include a rotor cap 36 that is configured to be attached to the rotor 34 so as to rotate with the rotor 34. The rotor cap 36 defines a proximal facing surface that abuts a distal facing surface on the proximal side of the damper housing 32. In one example, the proximal facing surface can be tapered as it extends in the proximal direction so as to define a point contact with the damper housing 32, thereby facilitating rotation of the rotor 34 with respect to the damper housing 32. In particular, the rotor cap 36, and thus the rotor 34 which is rotatably fixed to the rotor cap 36, can rotate with respect to the damper housing 32 about the point contact defined at the interface between the rotor cap 36 and the damper housing 32.

Figures 7, 8:
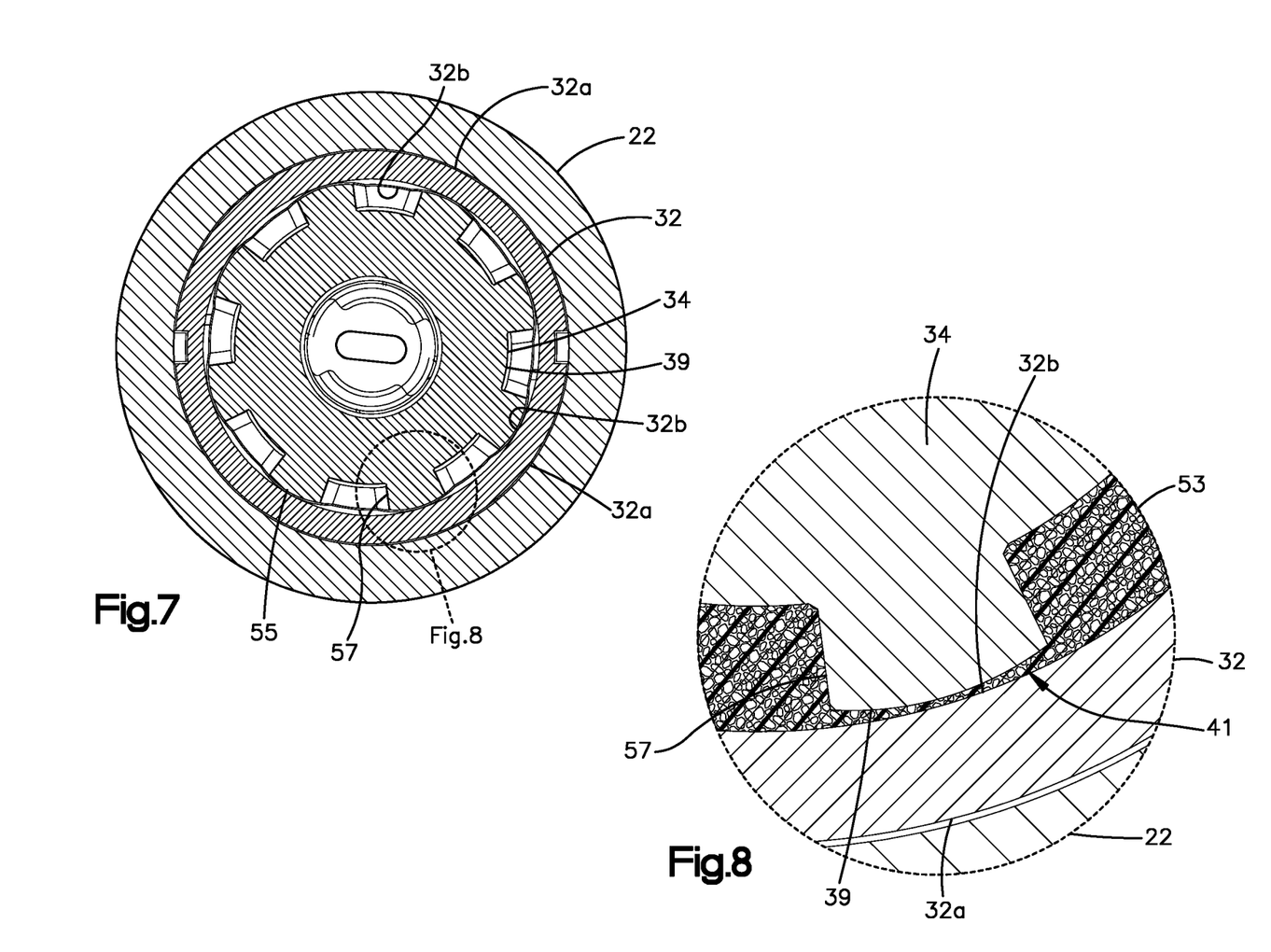
FIG. 7 is a cross-sectional view of the injection training device shown in FIG. 1A, showing a damper chamber between a rotor and a damper housing, wherein a viscous fluid is disposed in the damper chamber.
FIG. 8 is an enlarged portion of the cross-sectional view of the injection training device shown in FIG. 7.

Referring also to FIGS. 7-8, a damper chamber 41 is disposed between the outer surface 39 of the rotor 34 and the inner surface 32b of the damper housing 32 along a direction that is perpendicular to the axis 35. The direction perpendicular to the axis 35 can also be referred to as a radial direction in some examples. It is also envisioned that at least some of the components of the injection training device 20 define shapes that define lateral and transverse directions that are perpendicular to each other and perpendicular to the axis 35 which can be said to extend along a longitudinal direction. Thus, the radially outward and inward directions as described herein can alternatively be expressed as directions away from and toward, respectively, the axis 35 along one or both of the lateral direction and the transverse direction.

A viscous fluid 53 can be disposed in the damper chamber 41 that resists rotation of the rotor 34 with respect to the damper housing 32 about the axis 35. Further, the rotor 34 can have a textured radially outer surface 55 that faces the damper housing 32, and in particular faces the radially inner surface 32b of the damper housing 32. Thus, the textured surface 55 can at least partially define the damper chamber 41. The textured surface 55 defines variable distances from the radially outer surface of the rotor 34 to the radially inner surface 32b of the damper housing 32 along the radial direction. As the rotor 34 is driven to rotate with respect to the damper housing 32 about the axis 35, the viscous fluid 53 interferes with the motion of the textured surface 55, thereby further impeding rotation of the rotor 34. The textured radially outer surface 55 can include a plurality of knurls 57 that project radially outward toward the radially inner surface 32b of the damper housing 32. The knurls 57 can be spaced from each other along a plane that is oriented perpendicular to the axis 35. Thus, the knurls 57 can be circumferentially spaced from each other. The knurls 57 can further be oriented along a direction parallel to the axis 35. The rotor cap 36 can define a textured outer surface as described above with respect to the rotor 34.

Thus, the radially outer surface 39 of the rotor 34 can be textured and the radially inner surface 32b of the damper housing can be smooth in one example. Alternatively, the radially inner surface 32b of the damper housing can be textured such as knurled as described above with respect to the rotor 34, and the radially outer surface 39 of the rotor 34 can be smooth. Alternatively still, both the radially outer surface 39 of the rotor 34 and the radially inner surface 32b of the damper housing can both be textured, such as knurled, as described above with respect to the rotor.

Referring now to FIGS. 2-5, the rotor 34 can define an annular void 50 that extends into the distal end of the outer wall 37 along a proximal direction. Thus, the rotor 34 can define a radially inner wall 52 and the radially outer wall 37 that are radially separated from each other by the annular void 50. The radially inner wall 52 is spaced from the radially outer wall 37 in the radially inward direction. Further, the radially inner wall 52 can extend distally past the radially outer wall 37. The annular void 50 can be disposed at a distal portion of the rotor 34. The outer surface 39 at the distal portion of the rotor 34 can be radially outwardly offset with respect to the outer surface 39 at the proximal portion of the rotor 34. In this regard, the outer surface 39 of the rotor 34 can be substantially aligned with the radially outer surface of the plunger 24.

The rotor 34 is operably coupled to the threaded shaft 40, such that a force applied to the rotor 34 in the distal direction causes the rotor 34 to rotate in the first direction of rotation about the axis 35. In particular, referring also to FIG. 9, the threaded shaft 40 has an outer surface 43 that defines at least one thread 45. The at least one thread can be a helical thread. The clutch 42 further defines at least one thread 47 that is threadedly mated with the threaded shaft 40. Thus, the clutch 42 travels along the at least one thread 47 as the clutch travels in each of the proximal direction and the distal direction. Thus, when a force is applied to the clutch 42 in the distal direction, the clutch 42 rotates in a first direction of rotation about the axis 35 as the shaft travels along the threaded shaft 40. When a force is applied to the clutch 42 in the proximal direction, the clutch 42 rotates in a second direction of rotation about the axis 35 as the shaft travels along the threaded shaft 40 in the proximal direction. The second direction of rotation is opposite the first direction of rotation.

Figure 9:
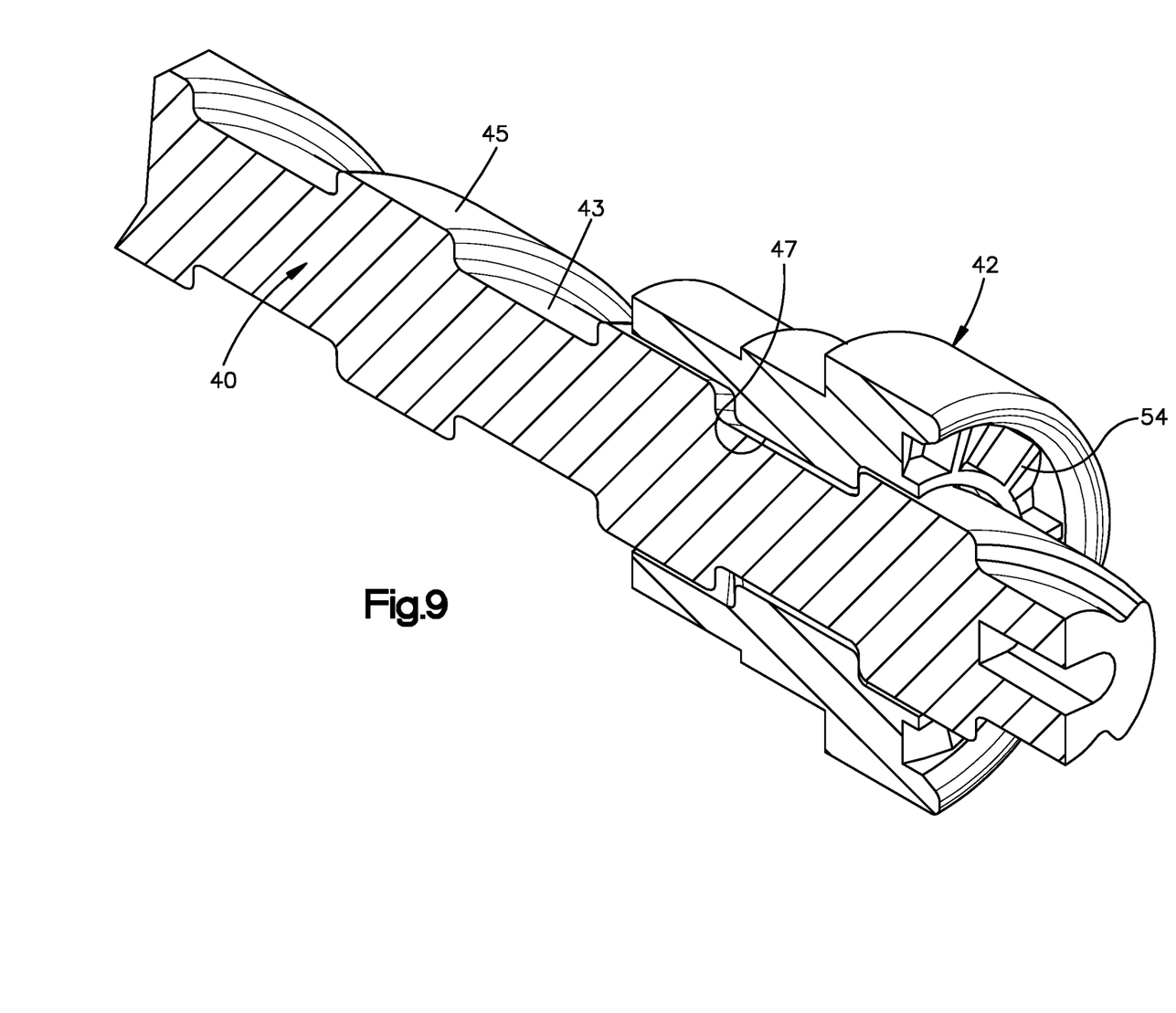
FIG. 9 is a cut-away perspective view of a clutch assembly of the injection training device shown in FIG. 1A.

It should be appreciated that while the clutch 42 is shown threadedly mated to the shaft 40, other variations are contemplated that cause the clutch 42 to rotate as it travels in the distal direction, and in the proximal direction. For instance, the radially outer surface of the clutch 42 can alternatively threadedly mate with a thread that is supported by the radially inner surface of the barrel 22. The device does not include the shaft 40 that extends through the barrel void 23 of the barrel 22 in this example. The internal barrel void 23 can contain a medication or other drug to be delivered to a patient. In this regard, a needle can be attached to the distal end of the barrel 22 using a Leur lock or the like in the traditional manner. The damper housing cap 46, rotor retainer cap 38, damper housing 32, or any suitable alternative structure can include a stopper at its distal end that travels in the distal direction in the barrel void 23 as the plunger 24 is depressed in the distal direction. Thus, depression of the plunger 24 in the distal direction causes stopper to drive the medication from the internal barrel void 23 into the needle. The medication can thus be delivered to a patient via the needle. Accordingly, it is appreciated that the device 20 can be configured as an injection training device as described above, or can alternatively be configured as an injection device in some examples.

Figure 5:
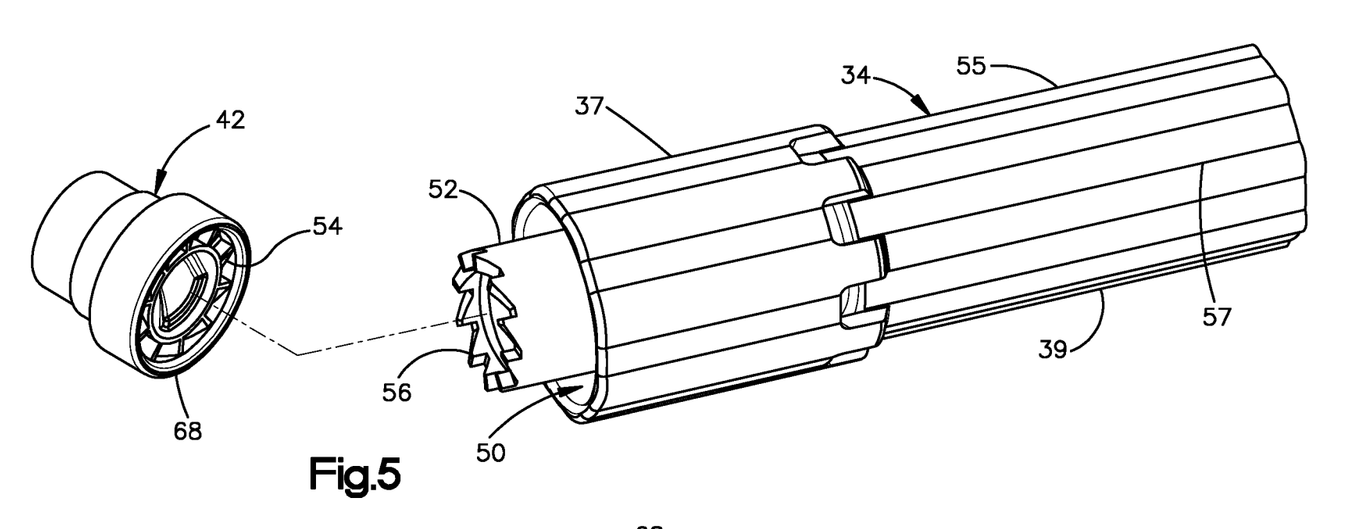
FIG. 5 is an exploded perspective view of a clutch and a rotor of the injection training device shown in FIG. 4.

Referring now also to FIG. 5, the clutch 42 is rotatably engaged with the rotor 34 in the first direction of rotation. Accordingly, rotation of the clutch 42 in the first direction of rotation drives the rotor 34 to rotate with the clutch 42 in the first direction of rotation. In particular, the clutch 42 can define at least one tooth 54 such as a plurality of teeth 54. The teeth 54 can extend from a surface of the clutch 42 in the proximal direction. In one example, the teeth 54 can extend from a proximal end of the clutch 42. Similarly, the rotor can define at least one tooth 56 such as a plurality of teeth 56 that are configured to engage the at least one tooth 54 of the clutch 42. The teeth 56 can extend from the distal end of the inner wall 52 of the rotor 34 in the distal direction. The teeth 54 and 56 can be configured to engage each other in the first direction of rotation. Thus, when the clutch 42 is driven to rotate in the first direction of rotation, the teeth 54 and 56 mate, and can interdigitate with each other, so as to rotatably fix the rotor 34 to the clutch 42. Therefore, as the clutch 42 rotates in the first direction of rotation, the rotor 34 rotates with the clutch 42 in the first direction of rotation.

With continuing reference to FIG. 5, at least one or both of the teeth 54 and 56 can be angled to ride past each other when the clutch rotates in the second direction of rotation. For instance, the teeth 56 of the rotor 34 and the teeth 54 of the clutch 42 can be sloped in the proximal direction as they extend in the second direction of rotation. Thus, the clutch 42 can be rotatably disengaged from the rotor 34 in the second direction of rotation, such that rotation of the clutch 42 in the second direction of rotation does not drive the rotor 34 to rotate in the second direction of rotation. Thus, the rotor can travel in the proximal direction without being driven by the clutch to rotate about the axis 35. In one example, the teeth 54 and 56 can slide along each other as the clutch is rotated in the second direction of rotation, thereby providing audible and/or tactile feedback to the user to indicate that the clutch is rotating in the second direction of rotation. Alternatively, the teeth 54 and 56 can be configured to rotatably fix to each other, such that the rotor 34 rotates with the clutch 42 in the second direction of rotation about the axis 35.

Referring again to FIGS. 2-4, the clutch 42 can be biased into engagement with the rotor 34 such that the clutch 42 abuts the rotor 34. In particular, the teeth 54 of the clutch 42 can abut the teeth 56 of the rotor 34. The injection training device 20 can include a biasing member 48 that provides a force against the clutch 42 in the proximal direction, thereby urging the clutch 42 into abutment with the rotor 34. Alternatively, the biasing member can bias the rotor 34 distally against the clutch 42. The biasing member 48 can be configured as a spring, such as a coil spring, an elastomer, or can be configured in accordance with any suitable alternative embodiment.

The biasing member 48 can be seated against any suitable spring seat 59 as desired. For instance, the injection training device 20 can include a damper housing cap 46 that defines the spring seat 59 in one example. The damper housing cap 46 can define an annular body 61 that defines a radially outer surface 63a and a radially inner surface 63b opposite the radially outer surface 63a. The damper housing cap 46 can be attached to the damper housing 32. For instance, the radially outer surface 63a of the damper housing cap 46 can be attached to the radially inner surface 32b of the damper housing 32. Thus, the damper housing cap 46 travels with the damper housing 32 in each of the proximal direction and the distal direction. In the event that the damper housing cap 46 and the damper housing 32 are metallic, the damper housing cap 46 can be welded to the damper housing 32. It should be appreciated that the damper housing cap 46 can be alternatively attached to the damper housing 32 as desired. The damper housing cap 46 can include the spring seat 59 that extends radially inward from the radially inner surface 63b of the damper housing cap 46. The spring seat 59 can be a proximal facing surface. The biasing member 48 can therefore be captured between the spring seat 59 and the clutch 42 in a compressed configuration, such that the biasing member 48 applies a force to the clutch 42 that biases the clutch 42 in the proximal direction. In some examples, the biasing member biases the clutch 42 against the rotor 34 such that the respective teeth 54 and 56 contact each other in the manner described above.

With continuing reference to FIGS. 2-4, the injection training device 20 is configured to seal the damper chamber 41 (see also FIG. 8). In particular, the injection training device 20 can include a rotor retainer cap 38 and a sealing gasket 44 that in combination prevent the viscous fluid 53 from leaking out of the damper chamber 41, and thus retain the viscous fluid 53 in the damper chamber 41. The rotor retainer cap 38 can be attached to the damper housing 32. For instance, the rotor retainer cap 38 can be attached to the damper housing 32 at a location distal of the damper chamber 41 and proximal of the damper housing cap 46. In one example, the rotor retainer cap 38 can be attached to the radially inner surface 32b of the damper housing 32. In the event that the rotor retainer cap 38 and the damper housing 32 are metallic, the rotor retainer cap 38 can be welded to the damper housing 32. It should be appreciated that the rotor retainer cap 38 can be alternatively attached to the damper housing 32 as desired. The rotor retainer cap 38 can travel with the damper housing 32 in each of the proximal direction and the distal direction.

In one example, the rotor retainer cap 38 can define a base 64 and an annular arm 66 that extends in the proximal direction from the base 64. The rotor retainer cap 38 can extend into the rotor 34 in the proximal direction. In particular, the arm 66 can extend into the annular void 50 of the rotor 34. The arm 66 can be radially spaced from the radially outer wall 37 and the radially inner wall 52 of the rotor 34, such that the rotor retainer cap 38 does not impede rotation of the rotor 34 during operation. The base 64 can be attached to the damper housing 32 in the manner described above. Thus, the viscous fluid in the damper chamber 41 is unable to flow in the distal direction from the damper chamber 41 through the interface between the rotor retainer cap 38 and the damper housing 32. The rotor retainer cap 38 can define a flange 65 that extends out from the base 64. The flange 65 can extend in the distal direction from the base 64 at a location radially inwardly spaced from the barrel 22, and radially outwardly spaced from the radially inner wall 52 of the rotor 34. The clutch 42 can include a finger 68, which can be an annular finger 68, that extends to a location between the rotor retainer cap 38 and the rotor 34. For instance, the finger 68 can extend to a location radially between the flange 65 and the rotor 34. In one example, the finger 68 can extend in the proximal direction to the location radially between the flange 65 and the rotor 34, and in particular the inner rotor wall 52. The finger 68 can be disposed radially outward with respect to the teeth 54 of the clutch 42.

Alternatively or additionally, the damper housing cap 46 can be attached to the rotor retainer cap 38. For instance, the proximal end of the damper housing cap 46 can be attached to one or both of the base 64 and the flange 65 of the rotor retainer cap 38. In one example, for instance when the rotor retainer cap 38 and the damper housing cap 38 and 46 are metallic, the rotor retainer cap 38 and the damper housing cap 46 can be welded to each other. Whether the damper housing cap 46 is attached to the rotor retainer cap 38, the damper housing 32, or both, the damper housing cap 46, the rotor retainer cap 38, and the damper housing 32 are all translatably and rotationally fixed to each other.

Figure 6:
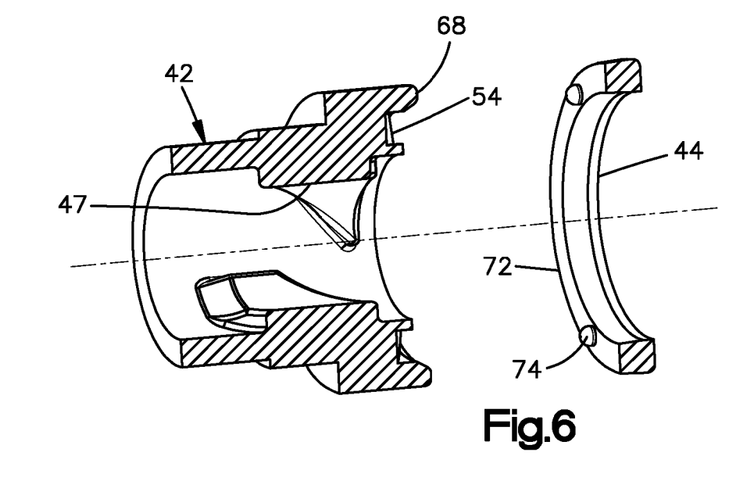
FIG. 6 is an exploded perspective view of the clutch shown in FIG. 5 and a sealing gasket.

Referring also to FIG. 6, the injection training device 20 can further include a sealing gasket 44 that seals an interface between the rotor retainer cap 38 and the rotor 34. The sealing gasket 44 is configured to prevent the viscous fluid 53 from leaking out of the damper chamber 41 at the interface between the rotor retainer cap 38 and the rotor 34. The sealing gasket 44 can include a ring-shaped body 72 (see also FIG. 2) that extends radially from the flange 65 of the rotor retainer cap 38 to the radially inner wall 52 of the rotor 34, thereby sealing the interface between the base 64 and the radially inner wall 52 with respect to the viscous fluid 53 that is disposed in the damper chamber 41. Accordingly, the rotor retainer cap 38 in combination with the sealing gasket 44 effectively seal the viscous fluid 53 in the damper chamber 41 during operation of the injection training device 20. The sealing gasket 44 can be under constant compression between the radially inner surface of the rotor retainer cap 38 and the radially outer surface of the rotor 34. The sealing gasket 44 can further include a plurality of localized bumps 74 that project from the body 72 in the distal direction. The localized bumps 74 can make point contact with the finger 68 of the clutch 42. The sealing gasket 44 can be made from any suitable elastomeric or other material as desired.

Referring again to FIGS. 2-4, it should be appreciated that the plunger 24, the damper housing 32, the rotor retainer cap 38, and the damper housing cap 46 can all be attached to each other with respect to translation as to define a first assembly 78. The first assembly 78 is translatable in each of the proximal direction and the distal direction with respect to the barrel 22 without rotating about the axis 35. Thus, the plunger 24, the damper housing 32, the rotor retainer cap 38, and the damper housing cap 46 can be rotatably fixed to each other. Further, the base 22 can be fixed to the damper housing 32 and the plunger 24 with respect to rotation.

Figure 11:
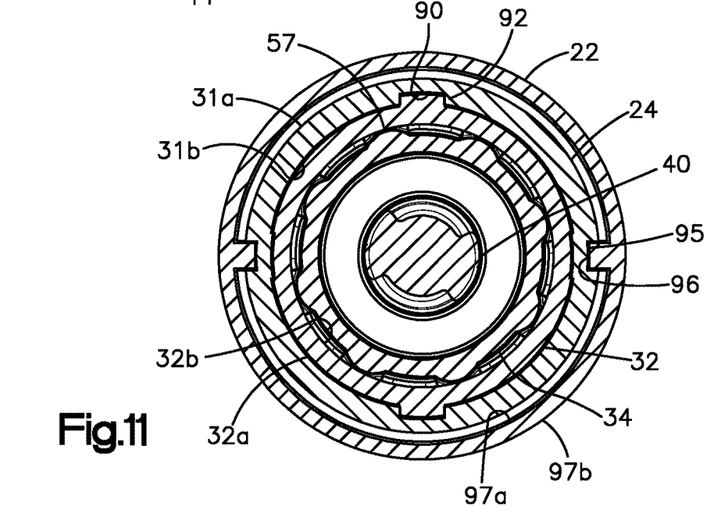
FIG. 11 is a sectional end elevation view of the injection training device taken along line 11-11 of FIG. 10.

In particular, referring now to FIGS. 2 and 11, the plunger 24 and the damper housing 32 are configured to interlock with each other so as to rotatably fix the plunger and damper housing 32 to each other. For instance, the plunger 24 and the damper housing 32 can define complementary engagement members that interlock with each other such that the plunger 24 and the damper housing 32 are rotatably fixed to each other. The plunger 24 defines a radially outer surface 31*a* and a radially inner surface 31*b* opposite the radially outer surface 31*a*. The plunger 24 can define at least one groove 90 that extends radially into the radially inner surface 31*b* and is elongate along the axial direction. The at least one groove 90 can include a plurality of grooves 90 that are circumferentially spaced from each other. The damper housing 32 can define at least one rib 92 that projects radially out from the radially outer surface 32*a*. The at least one rib 92 can include a plurality of ribs 92 that are circumferentially spaced from each other. The ribs 92 are complementary to the grooves 90, and are configured to be inserted into the grooves 90, respectively, so as to rotatably fix the plunger 24 to the damper housing 32 when the proximal end of the damper housing 32 is received in a distal end of the plunger 24. Alternatively, the damper housing 32 can define the at least one groove, and the plunger 24 can define the at least one rib. Alternatively still, it should be appreciated that the engagement members of the plunger 24 and damper housing 32 can be constructed in accordance with any suitable alternative embodiment as desired, and can include geometric cross-sectional shapes of the plunger 24 and the damper housing 32. Further, the distal end of the plunger 24 can alternatively be received in the proximal end of the damper housing 32.

With continuing reference to FIGS. 2 and 11, the base 22 can couple to either or both of the damper housing 32 and the plunger 24 so as to rotatably fix the base 22, the damper housing 32, and the plunger 24 to each other. In particular, either or both of the plunger 24 and the damper housing 32 can define a respective first engagement member, and the base 22 includes a second engagement member that interlocks with the first engagement member to rotatably fix the base 22, the damper housing 32, and the plunger 24 to each other. In one example, the plunger 24 defines at least one first slot segment 94*a* that extends into its radially outer surface 31*a*, and is elongate along the axial direction. The at least one first slot segment 94*a* can include a plurality of first slot segments 94*a* circumferentially spaced from each other. The damper housing 32 defines a second slot segment 94*b* that extends into its radially outer surface 32*a* and is elongate along the axial direction. The at least one second slot segment 94*b* can include a plurality of second slot segments 94*b* circumferentially spaced from each other. When the plunger 24 is coupled to the damper housing 32 such that the respective engagement members interlock, the first and second slot segments 94*a* and 94*b* are aligned, such that the first and second slot segments 94 and 95 combine to define at least one slot 95.

The first and second slot segments 94*a* and 94*b*, and thus the at least one slot 95, define respective engagement members that are configured to interlock with a complementary engagement member of the base 20 so as to rotatably fix the base 20 to each of the plunger 24 and the damper housing 32. In particular, the base 22 can include a projection 96 that projects radially inward from a radially inner surface 97*a* of the base 22 that is opposite a radially outer surface 97*b* of the base 20. The radially inner surface 97*a* faces the damper housing 32 when the plunger 24 is in the initial position, and faces the damper housing 32 and the plunger 24 when the plunger is depressed. The projection 96 rides in the slot 95 as the plunger moves between the initial undepressed position and the fully depressed position. Because the damper housing 32 and the plunger 24 are rotatably fixed to each other, the base 22 is also rotatably fixed to the first assembly both when the plunger 24 is in the undepressed position, and when the plunger 24 is in the depressed position. While in one example the engagement member of the plunger 24 and the damper housing 32 defines a slot, and the complementary engagement member of the base 22 defines a rib, it is recognized that the engagement members can be alternatively configured as desired. For instance, the engagement member of the base 22 can define a slot, and the engagement member of the plunger 24 and the damper housing 32 can define a projection.

Referring again to FIGS. 2-4, the rotor 34, the clutch 42, and the rotor cap 36 are rotatably fixed to each other at least with respect to the first direction of rotation so as to define a second assembly 82. The second assembly 82 is rotatable with respect to the first assembly 78 in the first direction of rotation. Further, the first and second assemblies 78 and 82 are configured to travel together with respect to the barrel 22 in each of the distal direction and the proximal direction.

Figure 10:
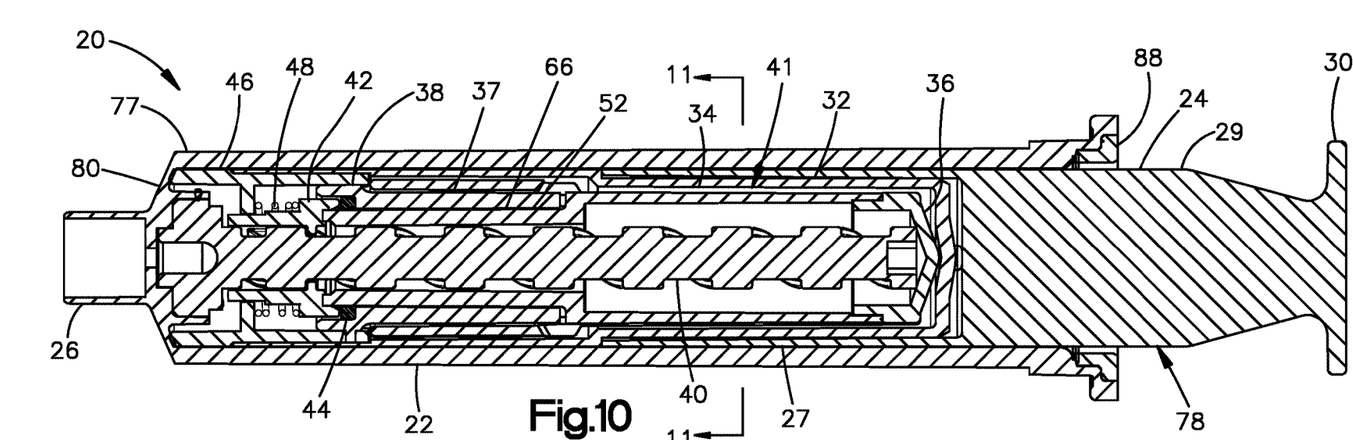
FIG. 10 is a sectional side elevation view of the injection training device in the final deployed position shown in FIG. 1B.

The first assembly 78 defines a first or distal stop assembly that prevents translation of the first assembly 78 in the distal direction once the injection training device has been moved to its fully deployed position. The distal stop assembly is defined by first and second distal stop members 73 and 75 that abut each other when the plunger 24 has moved to a fully depressed position. In one example, the first distal stop member 73 can be defined by a first distal stop surface 77 of the barrel 22. The first distal stop surface 77 can define a distal end of an internal annular gap 79 that extends in the distal direction into the barrel 22. The second distal stop member 75 can be defined by the damper housing cap 46. The second distal stop member 75 can define a second distal stop surface 80 that is configured to abut the first stop surface 77. The second distal stop surface 80 can be defined by a distal surface of the second distal stop member 75. As illustrated in FIG. 10, as the plunger 24 reaches the fully depressed position, the second distal stop member 75 is received in the internal annular gap 79 until the first and second distal stop surfaces 77 and 80 abut each other, thereby preventing further movement of the plunger 24 in the distal direction with respect to the barrel 22.

Referring again to FIGS. 2-4, the injection training device 20 further includes a second or proximal stop assembly that is configured to prevent movement of the plunger 24 in the proximal direction with respect to the barrel 22 when the plunger is 24 in the initial or undepressed position. The proximal stop assembly is defined by first and second proximal stop members 84 and 86 that abut each other when the plunger 24 is in the initial or undepressed position, thereby preventing the plunger from traveling in the proximal direction with respect to the barrel 22. In one example, the first proximal stop member 84 can be defined by the damper housing 32, and can project radially outward from the radially outer surface 32a of the damper housing 32. The first proximal stop member 84 defines a first proximal stop surface 85. The second proximal stop member 86 can be supported by the barrel 22. In particular, the injection training device 20 can include a retention member 88 that can be attached to, and thus supported by, the barrel 22. The retention member 88 can be disposed at a location in radial alignment with the barrel flange 28, or any suitable alternative location. The retention member 88 can define a second proximal stop surface 87 that faces the first proximal stop surface 85. When the plunger 24 is in the initial undepressed position, the first and second proximal stop surfaces 85 and 87 abut each other, thereby preventing movement of the plunger 24 in the proximal direction with respect to the barrel 22. Thus, the proximal stop assembly can prevent the plunger 24 from inadvertently backing out entirely from the barrel 22.

Operation of the injection training device 20 will now be described with reference to FIGS. 2-10 generally. As shown at FIGS. 2-4, the device begins in the first or undeployed position, whereby the plunger 24 is in the undepressed position. To simulate an injection, the user applies a deployment force to the plunger 24 in the distal direction sufficient to urge the first assembly 78 to translate in the distal direction with respect to the barrel 22. In one example, the first assembly 78 can be rotatably fixed, such that the plunger 24 and the damper housing 32 do not undergo rotation as they translate in the distal direction. Thus, movement of the first assembly 78 in the first direction can be pure translation. Translation of the first assembly 78, and in particular of the plunger 24, in the distal direction causes a force to be applied to the rotor 34 that causes the rotor 34 to travel in the distal direction as the rotor rotates within the damper housing 32 in the first direction of rotation about the axis of rotation 35. In particular, the rotor 34 applies the force in the distal direction to the clutch 42, thereby driving the clutch 42 to travel in the distal direction. As the clutch 42 travels in the distal direction, the threaded shaft 40 causes the clutch 42 to rotate in the first direction of rotation. As the clutch 42 rotates in the first direction of rotation, the teeth 54 and 56 (see FIG. 5) engage such that the rotor 34 rotates with the clutch 42.

As described above, and referring also to FIGS. 7-8, the rotor rotates with respect to the damper housing 32 in the first direction of rotation about the axis 35. The rotor 34 and the damper housing 32 define the damper chamber 41 that extends radially from the radially outer surface 39 of the rotor 34 to the radially inner surface 32b of the damper housing 32. The viscous fluid 53 disposed in the damper chamber 41 provides a rotational counterforce that resists rotation of the rotor 34, thereby also resisting the rotation of the clutch 42 in the distal direction, which thereby also provides a resistive force that resists movement of the plunger 24 in the distal direction. Accordingly, the user experiences a resistance when depressing the plunger 24 that simulates the resistance that will be experienced by the user when depressing the plunger 24 of the corresponding injection device to deliver medication. The user continues to depress the plunger against the resistance provided by the viscous fluid 53 until the plunger 24 has reached the fully depressed position illustrated in FIG. 10, whereby the first and second distal stop members abut each other, thereby preventing further movement of the plunger 24 in the distal direction. The resistance against the movement of the plunger 24 in the distal direction results in a time duration to move the plunger 24 from the initial undepressed position to the final fully depressed position. The time duration can simulate the time duration to fully deliver the medication from the corresponding injection device.

It should be appreciated that the injection training device 20 can be tuned to vary the resistance to movement of the plunger 24 in the distal direction, and also the resulting time duration to move the plunger 24 from the first undepressed position to the final fully depressed position. For instance, the viscosity of the viscous fluid 53 disposed in the damper chamber 41 can be adjusted to vary the counterforce to rotation of the rotor 34 with respect to the damper housing 32, and consequently the resistive force that resists depression of the plunger 24. A higher viscosity fluid will increase the resistance to rotation of the rotor 34 with respect to the damper housing 32, while a lower viscosity fluid will decrease the resistance to the rotation of the rotor 34 with respect to the damper housing 32. In one example, the viscous fluid can be DG4810 damping grease commercially available from Dongguan Vnovo Lubricants Technology Co., Ltd. having a place of business in Guangdong, China. The viscous fluid can have a viscosity of approximately 10,000 CST at 20 degrees C., though it is recognized that the injection training device 20 can be tuned to work with virtually any viscosity that resists rotation of the rotor 34 relative to the damper housing 32. Further, the size of the knurls 57, and thus the radial distance from the rotor 34 to the damper housing 32 can also impact the counterforce to rotation of the rotor 34. In general, greater radial distances from the rotor 34 to the damper housing 32 will decrease the counterforce to rotation of the rotor 34. In general, decreased radial distances from the rotor 34 to the damper housing 32 will increase the counterforce to rotation of the rotor 34. In one example, a proximal portion of the rotor 34 can have a different outer diameter than a distal portion of the rotor 34. For instance, the outer diameter of the proximal portion of the rotor 34 can be less than the outer diameter of the distal portion of the rotor 34. At the proximal portion of the rotor 34, a first proximal radial distance from the radially outermost surface of the knurls to the damper housing 32 can range from approximately 0.01 mm to approximately 0.3 mm, such as approximately 0.09 mm. At the proximal portion of the rotor 34, a second proximal radial distance from the radially outer surface of the rotor 34 between adjacent ones of the knurls to the damper housing 32 is greater than the first proximal radial distance. The second proximal radial distance can range from approximately 0.1 mm to approximately 0.7 mm, such as approximately 0.35 mm. At the distal portion of the rotor 34, a first distal radial distance from the radially outermost surface of the knurls to the damper housing 32 can range from approximately 0.01 mm to approximately 0.35 mm, such as approximately 0.12 mm. At the distal portion of the rotor 34, a second distal radial distance from the radially outer surface of the rotor 34 between adjacent ones of the knurls to the damper housing 32 is greater than the first distal radial distance. For instance, the second distal radial distance can range from approximately 0.15 mm to approximately 1 mm, such as approximately 0.59 mm. Alternatively, the outer diameter of the proximal portion of the rotor 34 can be greater than the outer diameter of the distal portion of the rotor 34. It is recognized that these distances can vary greatly depending on the viscosity of the viscous fluid. The term "approximately" as used herein with reference to a size, shape, distance, or other parameter can include the stated parameter as well as up to 10% greater than the stated parameter and up to 10% less than the stated parameter. Further still, one or both of the radially outer surface of the rotor 34 and the radially inner surface 32b of the damper housing 32 can be textured. Greater textured surface area will generally increase the counterforce to rotation of the rotor. Reductions in textured surface area will generally decrease the counterforce to rotation of the rotor 34.

The injection training device 20 is designed for the plunger 24 to be returnable to the initial undepressed position after it has travelled to a position distal of the undepressed position. In particular, once the plunger 24 has traveled to a position distal of the undepressed position, for instance the final fully depressed position, the user can apply a return force to the plunger 24. The return force is directed in the proximal direction, and urges the plunger 24 to move in the proximal direction with respect to the barrel 22 toward the initial undepressed position. The return force applied to the plunger 24 is also applied to the damper housing 32, which is coupled to the plunger 24 with respect to movement in the proximal direction, and to the damper housing cap 46 which is coupled to the damper housing 32 with respect to movement in the proximal direction. Movement of the damper housing cap 46 in the proximal direction causes the biasing member 48 to urge the clutch 42 to move in the proximal direction. As the clutch 42 is in contact with the rotor 34, movement of the clutch 42 in the proximal direction causes the rotor 34 to move in the proximal direction. Alternatively or additionally, the rotor cap 36 can be translationally fixed to the plunger 24. Thus, the rotor cap 36, which is attached to the rotor 34, can rotate with respect to the plunger 24, but translates with the plunger 24. Either way, translation of the plunger 24 in the proximal direction causes the clutch 42 and the rotor 34 to travel in the proximal direction.

As described above, because the clutch 42 is threadedly mated with the shaft 40, the threaded shaft 40 drives the clutch to rotate in the second direction of rotation as the clutch 42 moves in the proximal direction. However, because the teeth 54 of the clutch 42 and the teeth 56 of the rotor 34 are not coupled with respect to the second direction rotation, the teeth 54 slip over the teeth of the rotor 34 as the clutch 42 rotates in the second direction of rotation. Therefore, the clutch 42 does not drive the rotor 34 to rotate in the second direction of rotation. The rotor 34 consequently translates with the plunger 24 in the proximal direction without undergoing rotation in the second direction of rotation. It is envisioned that contact between the teeth 54 of the clutch 42 and the teeth 56 of the rotor 34 may cause the rotor 34 to undergo minor rotation, depending on the resistance provided by the viscous fluid 53, but such rotation should it occur is inconsequential. It can thus be said that the rotor is rotationally fixed as it translates in the proximal direction. Thus, the viscous fluid 53 does not provide a counterforce against travel of the plunger in the proximal direction.

In alternative embodiments, it is recognized that the teeth 54 and 56 can be rotatably fixed in the second direction of rotation, such that the rotor 34 rotates in the second direction of rotation with the clutch 42. Alternatively, the clutch 42 and the rotor 34 can be a single unitary component. In this embodiment, the viscous fluid 53 provides a rotational counterforce against rotation of the rotor 34 in the second direction of rotation with respect to the damper housing 32. The rotational counterforce creates a resistive force against movement of the plunger 24 in the proximal direction.

It should be noted that the illustrations and discussions of the embodiments and examples shown in the figures are for exemplary purposes only and should not be construed limiting the disclosure. One skilled in the art will appreciate that the present disclosure contemplates a range of possible modifications of the various aspects, embodiments and examples described herein. Additionally, it should be understood that the concepts described above with the above-described embodiments and examples may be employed alone or in combination with any of the other embodiments and examples described above. It should further be appreciated that the various alternatives described above with respect to one illustrated embodiment can apply to all other embodiments and examples described herein, unless otherwise indicated. Reference is therefore made to the claims.

What is claimed:

1. An injection training device comprising:
    a barrel;
    a first assembly including a plunger and a damper housing coupled to the plunger, wherein the first assembly is translatable with respect to the barrel; and
    a second assembly including a rotor, such that a damper chamber is defined between the rotor and the damper housing, wherein a viscous fluid is disposed in the damper chamber,
    wherein translation of the first assembly causes a force to be applied to the rotor that causes the rotor to rotate about an axis of rotation with respect to the damper housing, and the viscous fluid resists rotation of the rotor about the axis with respect to the damper housing.

2. The injection training device of claim 1, wherein the second assembly is rotatable with respect to the first assembly.

3. The injection training device of claim 1, wherein the first assembly is rotatably fixed.

4. The injection training device of claim 1, wherein translation of the plunger in a distal direction causes the rotor to rotate in a first direction of rotation.

5. The injection training device of claim 4, wherein translation of the plunger in the distal direction causes the rotor to travel in the distal direction as the rotor rotates in the first direction of rotation.

6. The injection training device of claim 4, wherein translation of the plunger in a proximal direction opposite the distal direction causes the rotor to travel in the proximal direction.

7. The injection training device of claim 6, wherein the rotor travels in the proximal direction without being driven to rotate about the axis.

8. The injection training device of claim 4, further comprising a helically threaded shaft operably coupled to the rotor, such that when the force is applied to the rotor in the distal direction, the helically threaded shaft causes the rotor to rotate in the first direction of rotation.

9. The injection training device of claim 8, wherein the second assembly further comprises a clutch that is threadedly mated with the helically threaded shaft, and is in engagement with the rotor.

10. The injection training device of claim 9, wherein the rotor applies the force in the distal direction to the clutch, thereby driving the clutch to travel in the distal direction, wherein the clutch rotates in the first direction of rotation along the helically threaded shaft as the clutch travels in the distal direction.

11. The injection training device of claim 9, wherein the clutch is rotatably engaged with the rotor in the first direction of rotation, such that rotation of the clutch in the first direction of rotation drives the rotor to rotate in the first direction of rotation, and the viscous fluid resists rotation of the rotor in the first direction of rotation.

12. The injection training device of claim 11, wherein the helically threaded shaft causes the clutch to rotate in a second direction of rotation opposite the first direction of rotation as the clutch travels in a proximal direction opposite the distal direction.

13. The injection training device of claim 12, wherein the clutch is rotatably disengaged from the rotor in the second direction of rotation, such that rotation of the clutch in the second direction of rotation does not drive the rotor to rotate in the second direction of rotation.

14. The injection training device of claim 9, further comprising a biasing member that provides a force against the clutch in a proximal direction opposite the distal direction, thereby urging the clutch into abutment with the rotor.

15. The injection training device of claim 14, wherein the biasing member comprises a coil spring.

16. The injection training device of claim 14, further comprising a damper housing cap that is attached to the damper housing, wherein the damper housing cap defines a seat for the biasing member that extends from the damper housing cap to the clutch.

17. The injection training device of claim 16, wherein the damper housing cap defines a stop surface that abuts the barrel so as to prevent further translation of the first assembly in the distal direction.

18. The injection training device of claim 1, further comprising a rotor retainer cap that is attached to the damper housing and extends into the rotor, and a seal member disposed at an interface between the rotor retainer cap and the rotor.

19. The injection training device of claim 1, wherein the rotor has a textured outer surface that faces the damper housing so as to define variable distances from the outer surface of the rotor and the damper housing.

20. The injection training device of claim 19, wherein the textured outer surface comprises a plurality of knurls that are spaced from each other along a plane that is oriented perpendicular to the axis.

21. The injection training device of claim 1, wherein the plunger and the damper housing of the first assembly are translatable with respect to the barrel, and translation of the plunger and damper housing of the first assembly causes the force to be applied to the rotor that causes the rotor to rotate about the axis of rotation with respect to the damper housing.

* * * * *